US006544441B2

(12) United States Patent
Wachtler et al.

(10) Patent No.: US 6,544,441 B2
(45) Date of Patent: Apr. 8, 2003

(54) ORTHO-PHENYLPHENOLATE CONCENTRATES

(75) Inventors: Peter Wachtler, Krefeld (DE); Hans-Peter Wirges, Krefeld (DE)

(73) Assignee: Bayer Aktiengesellschaft, Leverkausen (DE)

( * ) Notice: Subject to any disclaimer, the term of this patent is extended or adjusted under 35 U.S.C. 154(b) by 49 days.

(21) Appl. No.: 09/931,664

(22) Filed: Aug. 16, 2001

(65) Prior Publication Data

US 2002/0040977 A1 Apr. 11, 2002

(30) Foreign Application Priority Data

Aug. 17, 2000 (DE) .......................... 100 40 165

(51) Int. Cl.[7] .................. C09K 15/32; C09K 15/02; C09K 15/08
(52) U.S. Cl. ................. 252/400.61; 252/404; 252/383; 252/384
(58) Field of Search ............... 252/400.61, 404, 252/407, 383, 384, 385

(56) References Cited

U.S. PATENT DOCUMENTS

| 3,993,700 A | * | 11/1976 | Smith et al. | |
| 3,997,615 A | * | 12/1976 | Klein et al. | |
| 4,467,123 A | * | 8/1984 | Mayer et al. | 568/730 |
| 4,538,007 A | * | 8/1985 | Gabel et al. | 568/751 |
| 5,629,350 A | * | 5/1997 | Gartner | 514/736 |
| 6,362,152 B1 | * | 3/2002 | Young et al. | 510/386 |

FOREIGN PATENT DOCUMENTS

WO 00/36913 6/2000

OTHER PUBLICATIONS

W. Paulus, "Microbicides for the Protection of Materials," Chapman & Hall, (month unavailable) 1993, p. 170–174, 2–Phenyl–phenol–o–Phenyl–phenol (OPP).

* cited by examiner

Primary Examiner—Joseph D. Anthony
(74) Attorney, Agent, or Firm—Godfried R. Akorli; Diderico van Eyl

(57) ABSTRACT

The invention relates to frost-stable aqueous alkaline solutions of highly concentrated o-phenylphenol and to their use as preservatives.

8 Claims, No Drawings

ORTHO-PHENYLPHENOLATE CONCENTRATES

BACKGROUND

The invention relates to frost-stable aqueous alkaline solutions of highly concentrated o-phenylphenol and to their use as preservatives.

Orthophenylphenol (OPP) is an important active compound for preparing preservatives for protecting industrial materials such as, inter alia, glues or adhesives, concrete additives, cooling lubricants, pigment slurries. It is the intended function of preservatives for industrial materials to protect the treated products against microbial degradation. For this purpose, the preservatives have to be predominantly in the aqueous phase to reach the microorganisms living there. Accordingly, it is a precondition for preservatives to be effective that they are sufficiently water-soluble.

However, for preservatives based on phenolic active compounds, this is not always the case to the desired degree. Thus, for example, the solubility of the active compound o-phenylphenol (cf., for example, W. Paulus, "Microbicides for the Protection of Materials," Chapman & Hall, 1993, page 170 ff.) in neutral water is only 0.02% by weight. To incorporate this active compound without any problems into industrial materials, it is therefore necessary to pre-dissolve the microbially active compound first, to convert it into a form which is better suitable for further processing. In practice, this is usually achieved by preparing a solution in alkaline solutions (aqueous sodium hydroxide solution, aqueous potassium hydroxide solution), alcohols, glycols and the like, followed by addition of the required amount of the resulting liquid biocide product to the product to be protected. From application points of view, it is particularly advantageous to convert OPP into the corresponding phenolate by neutralization with bases (for example LiOH, NaOH, KOH, $Ca(OH)_2$), since the alkali metal salts or alkaline earth metal salts of OPP have a considerably better solubility in water than free OPP.

The method of forming a presolution in aqueous sodium hydroxide solution, a method which is already known and widely used, is associated with the problem that, with an increasing active compound content (calculated for OPP), even at relatively low OPP concentrations, solutions are obtained which have a crystallization point which is too high for practical application. Owing to crystallization, which in some cases occurs even at temperatures above 0° C., it is difficult to use such solutions in a controlled manner in industrial practice, in particular during the cold time of year, when undesirable solidification of the biocide product in storage tanks, pipelines and pumps may occur. This process requires time-consuming and costly measures for re-liquefying the biocide product and may result in production down-times. In addition, an uncontrolled solidification in pipelines and pumps may lead to a build up of pressure and leakages which, from the point of view of operational safety, causes a risk.

The tendency of aqueous solutions of o-phenylphenol (OPP) in aqueous NaOH to crystallize is shown in the table below

| OPP (% by weight) | Commencement of crystallization ° C. |
|---|---|
| 18.8 | −7 |
| 21.8 | −3 |
| 25.0 | 3.5 |
| 28.1 | 10 |

To provide more highly concentrated solutions of OPP in alkaline media, solutions in aqueous potassium hydride solution have been described, in addition to the solutions in aqueous sodium hydroxide solution described above. However, only mixtures of a maximum concentration of up to 30% by weight of OPP have been prepared and used commercially to date. In addition to the excess of alkali of the known 30% strength OPP solution, which is too high for many applications, the active compound content of this formulation is, with respect to optimum logistics, still too low, since shipping and internal company logistics require large quantities of water to be moved, which leads to an uneconomical operation and moreover appears to be worthy of improvement from an ecological point of view.

Accordingly, it is the object of the present invention to provide aqueous alkaline solutions of OPP which do not have the above-described disadvantages of the known solutions.

In particular, it is an object to provide more highly concentrated solutions (>30% by weight of OPP) of OPP in aqueous-alkaline media such as aqueous solutions of LiOH, NaOH, KOH or $Ca(OH)_2$ and binary mixtures of these alkaline media which remain stable for the duration of storage and use even at temperatures below 0° C., without any crystallization taking place.

Surprisingly, it has now been found that concentrated solutions of OPP salts in water, which are crystallization-stable (frost-stable) even at low temperatures, are obtained when the components are mixed in certain ratios.

SUMMARY

The invention relates to a mixture comprising (i) water, (ii) o-phenylphenol and (iii) a base component, wherein the o-phenylphenol and the base component are at a molar ratio ranging from 1:1.02 to 1:1.10 and the o-phenylphenol is present in the mixture at 45% by weight. The invention also relates to a process comprising (A) mixing (i) water, (ii) o-phenylphenol and (iii) a base component, and (B) forming a mixture comprising (i) water, (ii) o-phenylphenol and (iii) a base component, wherein the o-phenylphenol and the base component are at a molar ratio ranging from 1:1.02 to 1:1.10 and the o-phenylphenol is present in the mixture at 45% by weight. The invention also relates to a method comprising (A) treating an industrial material comprising water, o-phenylphenol and a base component, wherein the o-phenylphenol and the base component are at a molar ratio ranging from 1:1.02 to 1:1.10 and the o-phenylphenol is present in the mixture at 45% by weight, and (B) protecting the industrial material. These and other features, aspects, and advantages of the present invention will become better understood with reference to the following description and appended claims.

DESCRIPTION

The invention relates to a mixture comprising (i) water, (ii) o-phenylphenol and (iii) a base component, wherein the o-phenylphenol and the base component are at a molar ratio ranging from 1:1.02 to 1:1.10 and the o-phenylphenol is present in the mixture at 45% by weight. The invention also relates to a process comprising (A) mixing (i) water, (ii) o-phenylphenol and (iii) a base component, and (B) forming a mixture comprising (i) water, (ii) o-phenylphenol and (iii) a base component, wherein the o-phenylphenol and the base component are at a molar ratio ranging from 1:1.02 to 1:1.10 and the o-phenylphenol is present in the mixture at 45% by weight. The invention also relates to a method comprising (A) treating an industrial material comprising water, o-phenylphenol and a base component, wherein the o-phenylphenol and the base component are at a molar ratio ranging from 1:1.02 to 1:1.10 and the o-phenylphenol is present in the mixture at 45% by weight, and (B) protecting the industrial material.

Accordingly, the solutions according to the invention are prepared by mixing water, OPP and the base required for forming the OPP salt in certain ratios.

The base component can include one or more bases. Suitable bases for preparing the OPP concentrates according to the invention are in particular alkali metal hydroxides and alkaline earth metal hydroxides. Lithium hydroxide (LiOH), sodium hydroxide (NaOH), potassium hydroxide (KOH) and calcium hydroxide ($Ca(OH)_2$) may be mentioned by way of example.

Preference is given to using NaOH or KOH. It is also possible to use mixtures of the hydroxides mentioned, for example KOH/NaOH mixtures. A particularly preferred hydroxide is potassium hydroxide.

Surprisingly, it has been found that the object described can be achieved by mixing OPP and potassium hydroxide or OPP and potassium hydroxide/sodium hydroxide mixtures in a predetermined ratio and adjusting the concentration of OPP in the solution to the concentration required for achieving the object mentioned. Surprisingly, it is possible to prepare solutions having a content of more than 30% by weight of OPP, in particular highly concentrated OPP-K or OPP-K/Na solutions which are crystallization-stable even at low temperatures.

The OPP concentrates according to the invention are prepared, in particular, from (a) potassium hydroxide or potassium hydroxide/sodium hydroxide mixtures, (b) OPP and (c) water.

The molar ratio of o-phenylphenol to potassium hydroxide or to the sum of the molar proportions of potassium hydroxide/sodium hydroxide mixtures is from 1:1.01 to 1:1.5, preferably from 1:1.02 to 1:1.10.

The OPP content is from 30 to 55% by weight, in particular from 40 to 50% by weight. In a particularly preferred embodiment, the OPP content is 45%. It is calculated using the formula below:

$$\% \text{ by weight of OPP} = \frac{\text{Quantity of OPP}}{\text{Quantity of water} + \text{quantity of base} + \text{quantity of OPP}} \cdot 100$$

The OPP concentrates according to the invention are used as preservatives for industrial materials (cf., for example, W. Paulus "Microbicides for the Protection of Materials", Chapman & Hall, 1993, page 170 ff.) to protect them against microbial degradation. Examples of industrial materials which may be mentioned are glues, adhesives, concrete additives, sealing materials, cooling lubricants, printing thickeners, polymer dispersions, detergents and surfactants, wax emulsions and polishes, drill fluids, paints, bitumen emulsions and pigment slurries.

Advantageously, mixtures made in accordance to the invention are frost-stable at low temperatures. Generally, a mixture prepared in accordance with the invention will be frost-stable (will not crystallize) at a temperature that is below 0° C.

The invention is further described in the following illustrative examples in which all parts and percentages are by weight unless otherwise indicated.

EXAMPLES

Example

Frost-Stable o-phenylphenol/potassium Concentrate a) At 20° C., 500.0 g of o-phenylphenol (=50% by weight of OPP) were added with stirring to a solution of 312.0 g of demineralized water and 188.0 g of KOH (91.9% pure), and the mixture was stirred until a clear solution was obtained. The solution was then cooled with stirring until crystallization commenced. After the crystallization had ended, the mixture was heated again slowly. The temperature at which the last crystals dissolve is the solubility temperature. For the solution of this composition, a solubility temperature of +4° C. was found, i.e. such a solution does not meet the objects of the invention.

b) At 20° C., 450.0 g of o-phenylphenol (=45% by weight of OPP) were added with stirring to a solution of 380.8 g of demineralized water and 169.2 g of KOH (91.9% pure), and the mixture was stirred until a clear solution was obtained. The solution was then cooled with stirring until crystallization commenced. After the crystallization had ended, the mixture was heated again slowly. The temperature at which the last crystals dissolve is the solubility temperature. For the solution of this composition, a solubility temperature of <−20° C. was measured, i.e. such a solution contains a considerably higher content of OPP than the solutions of the prior art and, at the same time, can be handled safely even at low temperatures.

Although the present invention has been described in detail with reference to certain preferred versions thereof, other variations are possible. Therefore, the spirit and scope of the appended claims should not be limited to the description of the versions contained therein.

What is claimed is:

1. A method comprising treating an industrial material by adding to said industrial material a mixture comprising water, o-phenylphenol and a base component, wherein the o-phenylphenol and base component are at a molar ratio ranging from 1:1.02 to 1:1.10 and the o-phenylphenol is present in the mixture at 45% by weight, and protecting the industrial material.

2. The method according to claim 1, wherein the base component is selected from the group consisting of alkali metal hydroxides and alkaline earth metal hydroxides, and mixtures thereof.

3. A mixture comprising (i) water, (ii) o-phenylphenol and (iii) a base component, wherein the o-phenylphenol and the base component are at a molar ratio ranging from 1:1.02 to 1:1.10 and the o-phenylphenol is present in the mixture at 45% by weight.

4. The mixture of claim 3, wherein the base component is selected from the group consisting of alkali metal hydroxides, alkaline earth metal hydroxides, and mixtures thereof.

5. The mixture according to claim 3, wherein the mixture is a preservative for an industrial material.

6. A process comprising:
(A) mixing (i) water, (ii) o-phenylphenol and (iii) a base component, and
(B) forming a mixture comprising (i) water, (ii) o-phenylphenol and (iii) a base component, wherein the o-phenylphenol and the base component are at a molar ratio ranging from 1:1.02 to 1:1.10 and the o-phenylphenol is present in the mixture at 45% by weight.

7. The process according to claim 6, wherein the base component is selected from the group consisting of alkali metal hydroxides and alkaline earth metal hydroxides, and mixtures thereof.

8. The process according to claim 6, wherein the mixture is a preservative for an industrial material.

* * * * *